United States Patent
Wöss

[11] Patent Number: 5,247,834
[45] Date of Patent: Sep. 28, 1993

[54] DENSITY MEASURING APPARATUS

[75] Inventor: Gerhard Wöss, Graz, Austria

[73] Assignee: AVL Gesellschaft fuer Verbrennungskraftmaschinen und Messtechnik GmbH. Prof. Dr.Dr. h.c. Hans List, Austria

[21] Appl. No.: 651,947

[22] Filed: Feb. 9, 1990

[30] Foreign Application Priority Data

Feb. 9, 1990 [AT] Austria .................. 301/90

[51] Int. Cl.$^5$ .............................. G01N 9/10
[52] U.S. Cl. .............................. 73/453; 73/452
[58] Field of Search .............. 73/448, 451, 452, 453, 73/454, 304 C, 305, 309, 718, 313, 314; 137/398; 324/661

[56] References Cited

U.S. PATENT DOCUMENTS

| | | | |
|---|---|---|---|
| 3,688,588 | 9/1972 | Hill | 73/451 |
| 3,726,128 | 4/1973 | Fiet | 73/453 |
| 4,131,019 | 12/1978 | Krauss | 73/453 |
| 4,134,301 | 1/1979 | Erwin, Jr. | 73/453 |
| 4,357,834 | 11/1982 | Kimura | 73/718 |
| 4,428,232 | 1/1984 | Tanaka et al. | 73/304 C |
| 4,454,761 | 6/1984 | Coulange | 73/305 |
| 4,476,723 | 10/1984 | Bryne | 73/453 |
| 4,785,669 | 11/1988 | Benson et al. | 73/718 |
| 5,001,927 | 3/1991 | LaCava et al. | 73/304 C |
| 5,111,698 | 5/1992 | Banholzer et al. | 73/718 |

FOREIGN PATENT DOCUMENTS

| | | | |
|---|---|---|---|
| 700314 | 12/1940 | Fed. Rep. of Germany | 73/453 |
| 3632019A1 | 3/1988 | Fed. Rep. of Germany | |
| 765705 | 9/1980 | U.S.S.R. | |
| 2169414 | 7/1986 | United Kingdom | 73/453 |

OTHER PUBLICATIONS

Haynes et al., "Differential capacitance sensor as position detector for a magnetic suspension densimeter", Rev. Sci. Instrum. 50(9), Sep. 1979 pp. 1154–1155.

Primary Examiner—Hezron E. Williams
Assistant Examiner—Michael Brock
Attorney, Agent, or Firm—Hill, Steadman & Simpson

[57] ABSTRACT

A simple and mechanically-rugged calculation or monitoring of the density of fluids, particularly of fuels serving the purpose of driving an internal-combustion engine, provides that a buoyant member is immersed into the fluid under examination, the buoyancy thereof being balanced out via a load applied with a spring. A capacitor that is dependent on the buoyancy and, therefore, on the density of the fluid under examination is formed between the buoyant member and the housing that holds the spring and is filled with the fluid under examination, the capacitor being monitored via a circuit arrangement.

13 Claims, 4 Drawing Sheets

DENSITY MEASURING APPARATUS

BACKGROUND OF THE INVENTION

1. Field of the Invention

The present invention relates to a measuring apparatus for determining the density of fluids, comprising a buoyant member immersed in the fluid to be investigated and having a known specific weight, whose buoyancy is balanced out via a loading device having a progressively-acting counterforce, and a measuring instrument for the vertical position of the buoyant member which comprises a capacitor which is variable in its value of capacitance corresponding to the vertical position of the buoyant member and an arrangement for monitoring the value of capacitance that serves as a measure for the fluid density.

2. Description of the Prior Art

Measuring apparatus for determining the density of fluids that work upon utilization of the bouyancy of a measuring member are known in the art, for example, in the form of an aerometer or, respectively, of the Mohr-Westphal balance, while utilizing the Archimedean principle, allow relatively simple and accurate density calculations under defined, standardized preconditions. In the known embodiments of such apparatus, problems arise, first of all, by reading or, respectively, further interpretation of the measurement results and, secondly, by measurements of fluids whose density changes in time-dependent fashion, so that, for example, the measurement of flowing fluids whose densities change over time is not possible or is only possible with disproportionately great expense.

In order to be able to determine density changes essentially continuously and of a fluid at least flowing with a certain flow rate as well, the Soviet Union patent document SU-A-765 705, for example, discloses a measuring device of the type initially set forth that works in a buoyancy-dependent manner and that is fashioned such that the fluid under investigation flows through a specimen container from the bottom to the top, whereby the buoyant member immersed into the fluid is balanced out via a suspension wire with a load device arranged outside of the specimen container. Whereas the suspension wire is guided with a constant radius relative to the pivot point of the load device independently of the buoyancy-dependent position of the buoyant member, the suspension of a counterweight at the load device is executed such that the effective lever arm increases linearly with increasing immersion depth of the buoyant member, so that the vertical position thereof in the fluid provides a direct measure for the respective density of the fluid. In addition to being identified by reading a scale, the respective density can also be identified with this known apparatus via a variable disk capacitor adjusted with the load device or, respectively, via the capacitance thereof.

The German patent document DE-A1-36 32 019, for example, discloses a device for measuring the density, whereby a measuring spindle is immersed into a measuring chamber, and a proximity switch that outputs an analog signal proportional to the density of the fluid is attached under the measuring spindle.

Although a continuous monitoring of the density of even flowing fluid is possible with such apparatus, disadvantages result. For example, the mechanical execution, having a buoyant member suspended via a long, freely-swinging suspension and having a load weight or a floating measurement spindle requires great care in the implementation of the measurement or in the stabilization of the overall measuring instrument. This is necessary since only the stationary utilization of the stabilized measuring instrument is meaningful, particularly for more accurate calculations of density. The same disadvantages, moreover, are also present in view of the initially-mentioned, previously-known modifications of density measuring equipment that work upon the utilization of the Archimedean principle. This results in certain employments of density measurements at fluids that are currently critical cannot be undertaken with the aforementioned, known apparatus.

In recent years, therefore, the continuous monitoring or, respectively, calculation of the density of the fuel supplied, for example, to an internal-combustion engine has become particularly critical since this can be additionally employed as a parameter in electronically-controlled ignition systems. Therefore, for example, specifically lighter fuel is employed in northern European countries than in southern European countries. There is also usually a difference in density between what are referred to as summer fuels and winter fuels. When, for example, what is referred to as the blocking quantity (corresponds to "wide-open throttle") is designed such that the respective internal-combustion engine produces its full power given light-weight fuel, it will then smoke given heavy fuel and vice-versa. The maximum injection amount could be adapted to the fuel present in the fuel tank via density monitoring. For the above reasons, however, the mentioned, known arrangements are not suitable for introduction into and for operation in, for example, a truck.

An electronic density measuring device was, in fact, disclosed some time ago in which the fluid to be investigated is sucked into a bent U-shaped glass tube that, excited to mechanical oscillations in the KHz range, serves a resonator. The resonant frequency is then a measure for the density of the fluid located in the glass tube. Although such a measuring device can, of course, also be fundamentally introduced into a motor vehicle or the like and could be used for monitoring the density of the fuel serving for drive, there are critical disadvantages. Not only are the mechanical structure of the resonator tube (tolerances) and the oscillatory excitation and evaluation involved, but also a separate pump would also usually be necessary for sucking the fuel under investigation through the measuring instrument. This would cause high overall added expense, particularly for mass employment in, for example, production-line passenger automobiles and which, therefore, is economically unjustifiable.

SUMMARY OF THE INVENTION

Proceeding on the basis of the above considerations, the object of the present invention is to provide a simple measuring apparatus of the type initially set forth such that the mentioned disadvantages of the known devices of this type are avoided and such that, in particular, the density of fluids can be reliably monitored, particularly in a cost-effective manner that, therefore, is also suitable for mass employment, even under relatively rugged mechanical environmental conditions such as alternating accelerations, vibrations and the like.

The above object is achieved, according to the present invention, in that the load device comprises a spring that presses against the bouyant member, the spring being secured to a housing which surrounds the buoyant member and the spring. The housing is filled with the electrically non-conductive fluid under examination. The capacitance of, first of all, the buoyant member and, secondly, of the housing is formed. The buoyant member, together with the load device (what is always to be understood by the term load device is the device that offers the force opposing the buoyancy), on the one hand, and the variable capacitor for monitoring the position of the buoyant member, on the other hand, are therefore accommodated in the housing that also contains the fluid under examination, this yielding an extremely compact and rugged structure of the measuring instrument. All movable parts are therefore completely surrounded by the fluid under examination, this yielding excellent damping. In addition, the buoyant member, in a preferred embodiment, can also be provided with damping wings as needed for damping undesired movement. The overall arrangement can be manufactured in an extremely cost-effective manner and, for example, can be arranged in the region of the outlet of the fuel tank of a motor vehicle or the like and the fuel to be examined can flow therethrough.

According to a preferred embodiment of the invention, it is provided that the spring is formed by a leaf spring and that the housing comprises a carrier member holding the leaf spring that embraces the leaf spring together with the buoyant member in a U-shaped configuration and comprises at least one cooperating electrode in the region of a conductive vane arranged at the buoyant member and forming an electrode of the capacitor. This yields an embodiment that is very simple in structural terms and is mechanically rugged, whereby the moving parts are optimally protected by the housing surrounding these parts. For example, this can then also be directly arranged at a suitable location in the fuel tank.

In this latter context, it is also provided in a particularly preferred, further development of the invention that the carrier member has its outside surrounded with a finely-perforate covering, particularly a fine-mesh, electrically-conductive screen. This thus enables a constant exchange or, respectively, flow through of the fluid to be investigated and it is simultaneously assured that wave motions or higher flow rates in the fluid under examination caused by other external conditions can have no influence on the movement or, respectively, on the position of the buoyant member. At the same time, contamination due to suspended particles in the fluid under examination is avoided and an electrical shielding of the variable capacitor is effected.

In a further development of the invention, true cooperating electrodes of the capacitors can be arranged at the housing or, respectively, at the carrier member, their difference in terms of capacitance values being identifiable as a measure of the density. The identification of the density is therefore reduced to the more sensitive calculation of a difference in capacitance value, this allowing an enhancement of the measuring accuracy in the most simple manner.

In another development of the invention, the spring of the load device can also be formed by a coil spring that is suspended in the upper region of the housing and carries a buoyant member, whereby the floor of the housing that is closed, except for the admission and outlet of the fluid to be examined, the floor forming the cooperating electrode of the capacitor, is constructed as a spherical cap having its center in the suspension of the coil spring. This development guarantees the measuring accuracy of the device in a simple manner, even within the standard longitudinal and transverse slants of, for example, motor vehicles, such as, for example, passenger cars, since the spacing of the buoyant member from the floor that forms the cooperating electrode of the capacitor does not change even given a longitudinal or transverse slant of the integrated measuring device.

Given the above-mentioned development, the admission of the fluid to be examined can preferably be arranged in the floor region of the housing, preferably tangentially aligned, whereby the outlet lies in the uppermost region of the housing. As a result thereof, no air bubbles that directly influence the variable capacitor or, respectively, the position of the buoyant member can form or, respectively, remain in the housing. As a result of the large flow cross section in the lower region of the housing, the inflow rate is so low, in addition, that the pendularly-suspended buoyant member cannot be disturbed by the flow.

According to a particularly preferred, further development of the invention, it can also be provided in this latter embodiment that the floor region is transmissive in a sieve-like manner and directly forms the admission, this likewise having positive influences in view of avoiding any and all disturbing movements of the buoyant member.

It can be provided in a particularly preferred embodiment of the invention that a compensation electrode that is stationary relative to the housing is arranged in the housing for taking the dependency of the measured value of capacitance on the dielectric constant of the fluid under examination into consideration and is connected to the arrangement for monitoring the capacitance. The dielectric constant that, for example, may also change together with the fuel density or, respectively, the influence thereof on the measured value capacitance can also be taken into consideration.

In a particularly preferred development of the invention, the capacitance between the buoyant member and the housing is a component of a fed back, capacitive bridge circuit, this allowing accurate measurements of the variable value of the capacitance and, therefore, of the density to be identified in a simple manner.

In order to suppress the influence of the dielectric constant E of the fluid under examination, at least one compensating capacitor can be arranged in that half of the measuring bridge containing the capacitor or capacitors that is or are variable in view of their value of capacitance in a further development of the invention. Since the variable capacitor of the invention lies fully in the fluid under examination, its value, as mentioned, is dependent not only on the buoyancy-dependent excursion of the buoyant member, but is also dependent on the value E of the fluid under examination. The sensitivity (output voltage difference per density difference) would thus be greater given a fluid having a higher E value. This influence of the E value can be suppressed with the mentioned compensation capacitor that is also a multi-part structure, as needed.

In a further development of the invention, the capacitance between the buoyant member and the housing can also be a frequency-influencing component part of an oscillator circuit whereby the density to be calculated or, respectively, to be monitored can be observed or, respectively, derives from the frequency detuning.

What all of the mentioned embodiments of the invention have in common is the simple and rugged execution or, respectively, design of the density measurement based on the Archimedean principle, this particularly enabling the cost-effective mass utilization of measuring instruments constructed in this manner for example, ongoing density measurement in the fuel of internal-combustion engines utilized in vehicles.

BRIEF DESCRIPTION OF THE DRAWINGS

Other objects, features and advantages of the invention, its organization, construction and operation will be best understood from the following detailed description, taken in conjunction with the accompanying drawings, on which.

DESCRIPTION OF THE PREFERRED EMBODIMENTS

Figure 1:
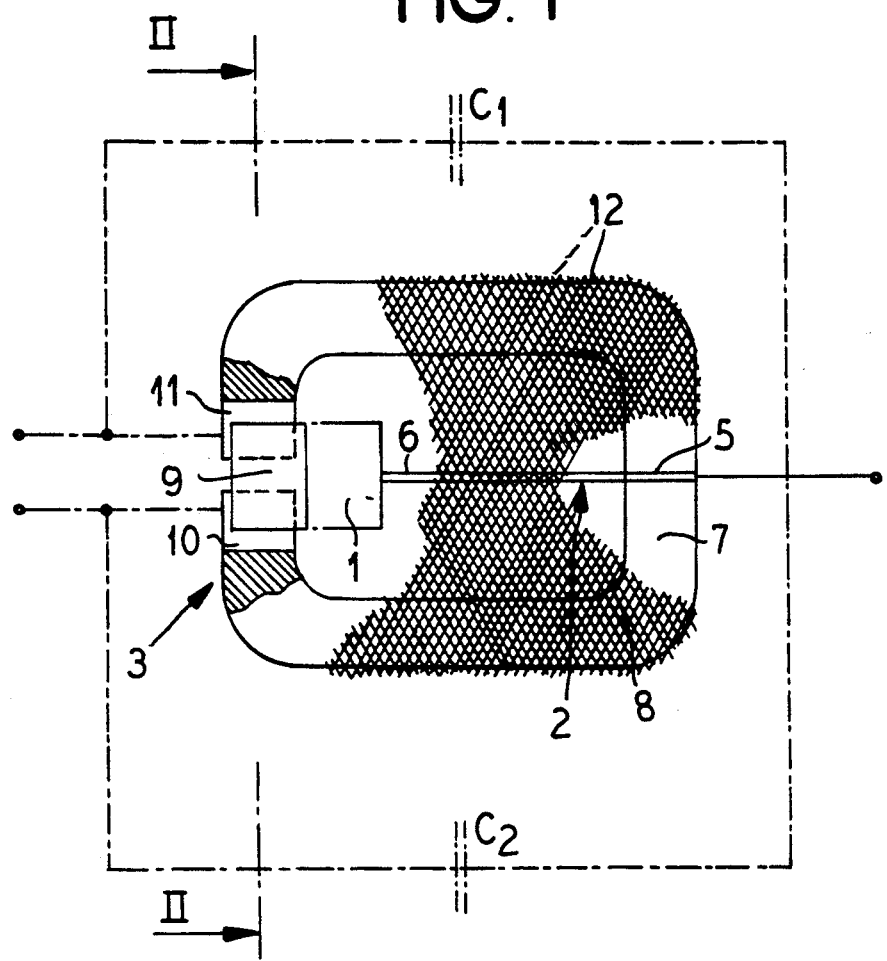
FIG. 1 is a partially cut side view of a component of the measuring device constructed in accordance with the present invention.
Figure 2:
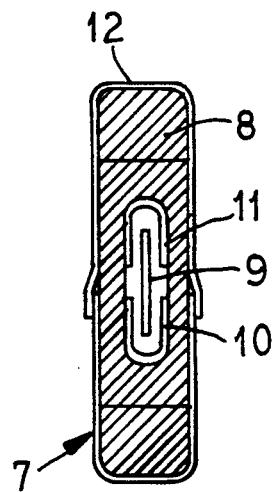
FIG. 2 is a sectional view of the device taken along the parting line II—II of FIG. 1.
Figure 3:
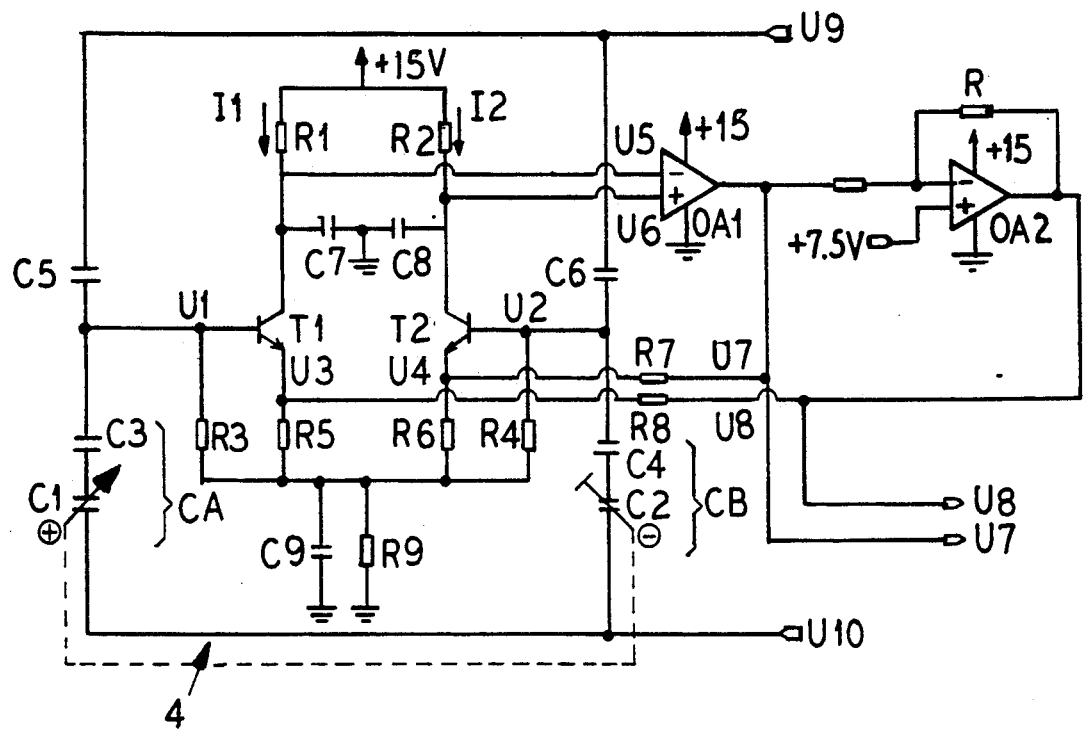
FIG. 3 is a schematic circuit diagram of an exemplary embodiment of a monitoring arrangement shown without the arrangement of FIGS. 1 and 2 for the capacitor that is variable in terms of its value capacitance.

A measuring apparatus for calculating the density of fluids, shown overall essentially in FIGS. 1–3, comprises a buoyant member 1 having a known, specific weight that is immersed in the fluid under examination, the buoyancy thereof (acting in the vertically-upward direction in the plane of the drawing when built into the fluid that is not shown here) is balanced out via a load device 2 having a progressively-acting counter force, and also comprises a measuring arrangement 3 for measuring the vertical position of the buoyant member 1. The measuring arrangement 3 comprises a capacitor C1, C2 (differential capacitance) that is variable in terms of its value of capacitance ($c_I$, $c_{II}$) corresponding to the position of the buoyant member 1 and comprises an arrangement 4 illustrated in FIG. 3 for monitoring the values $c_I$, $c_{II}$ of the capacitances that serve as a measure for the density.

The load device 2 comprises a spring 5 that presses against the buoyant member 1 and that, according to FIG. 1, is formed by a leaf spring 6. The spring 5 is secured to a housing 7 which surrounds the buoyant member 1 and the spring 5. The housing 7 is filled with an electrically-nonconductive fluid to be investigated. The housing 7 comprises a carrier member 8 holding the leaf spring 6 that embraces the leaf spring 6 together with the buoyant member 1 in a U-shaped configuration and comprises two cooperating electrodes 10, 11 in the region of a conductive vane 9 that is arranged at the buoyant member 1 and forms an electrode of the capacitor C1, C2. The capacitor C1, C2 is therefore defined, on the one hand, by the buoyant member 1 or, respectively, the vane 9 thereof and, on the other hand, by the housing 7 or, respectively, by the cooperating electrodes 10, 11 in the form of a difference between the values $c_I$, $c_{II}$ of the capacitance of the capacitors C1 and C2 and can be advantageously identified via the circuit-arrangement illustrated in FIG. 3 which shall be referred to below.

At its exterior, the carrier member 8 of the housing 7 according to FIG. 1 is surrounded by a finely-perforate covering 12 in the form of a fine-mesh, electrically-conductive screen, so that, in particular, the interior that accepts the buoyant member 1 and the spring 5 is protected against wave motions of the fluid under examination, whereby the continuous replacement of the fluid is nonetheless guaranteed. It may be seen from FIG. 2 in this context that the covering 12 completely surrounds the electrically-nonconductive carrier member 8 so that an electrical shielding for the internally-disposed cooperating electrodes 10, 11 and for the vane 9 or, respectively, for the capacitors formed therewith is also established.

Proceeding, for example, on the basis of the utilization of an illustrated arrangement for measuring or, respectively, monitoring the density of diesel fuel that amounts to between 0.8 and 0.9 kg/l at 15° C., dependent on the fuel composition, and that is also dependent on temperature, the buoyant member 1 is constructed with a specific weight of 0.85 kg/l (the mean density of the fuel). When the density of the fuel that is in fact present is higher than 0.85 kg/l, then the spring 5 is bent out in the upward direction by the buoyant member 1; given densities below 0.85 it is bent downwardly. The spring excursion is therefore a measure for the density of the fluid.

According to FIG. 3, the two capacitors C1 and C2 are components of a fed back, capacitive bridge circuit that is supplied with two diametrically-opposed voltages U9 and U10 via a square-wave oscillator (not shown). The values of capacitance for the bridge circuit are:

C5 = C6 (for example, 10pF); and
C3 = C4 (for example, 10pF).

The values $c_I$, $c_{II}$ of capacitance of the capacitors C1 and C2 lie on the order of magnitude of a few pF, whereby C2 is a trimmer capacitor.

Figure 3A:
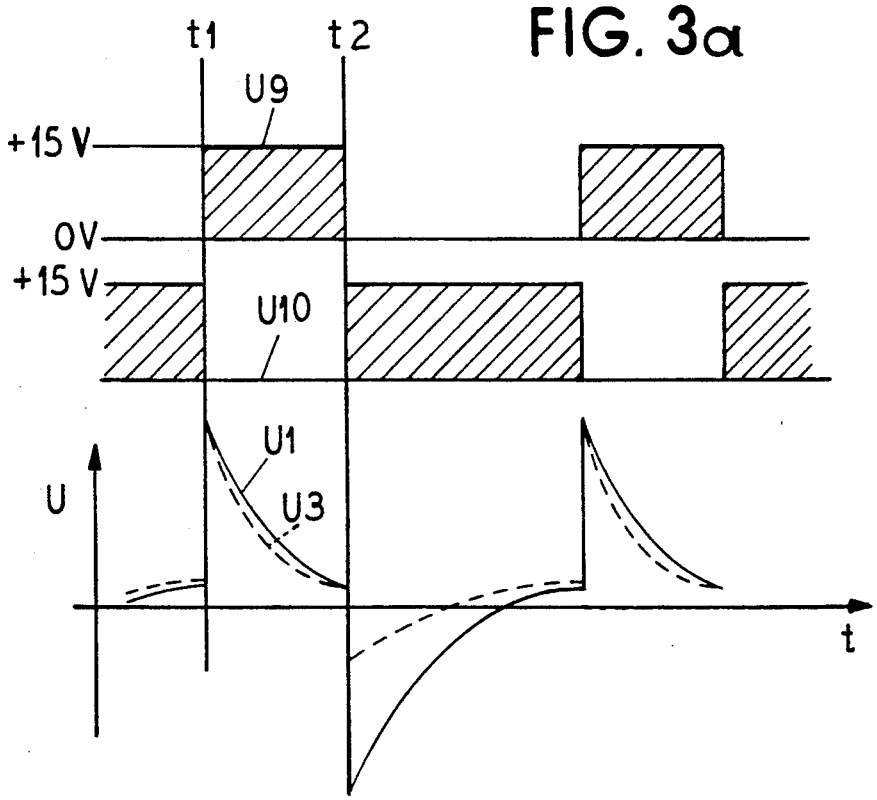
FIG. 3a is a voltage diagram directed to the circuit of FIG. 3.

The bridge lies at the square-wave voltages U9 and U10 (FIG. 3a).

The operation of the circuit shall be set forth below with the assistance of the events given the appearance of the edges of these square-wave voltages: Consideration of the symmetrical relationships at the bridge ($c_I = c_{II}$).

Given complete symmetry, all voltages and currents in the two bridge branches are identical i.e. the voltages U5 and U6 smoothed with the capacitors C7 and C8 are of the same size; the voltages U7 and U8 are likewise of the same size and here have the quiescent value of +7.5 volts. Due to the symmetry, only the left-hand part of the bridge shall be described below.

At the time t1, the voltage U9 has a positive edge and the voltage U10 has a negative edge.

As a result of the capacitor C5 being greater than the capacitance of the capacitor CA (C1+C3), the voltage U1 decreases exponentially. The voltage U3 follows shifted by the base-emitter voltage. Corresponding to the voltage U3, an emitter current that can likewise be taken flows and this divides onto the resistors R5 and R8.

At the time t2, the voltage U9 has a negative edge and the voltage U10 has a positive edge. The voltage U1 becomes negative and the transistor T1 is inhibited.

The emitter current generated between the time t1 and the time t2 yields the collector current that is smoothed via the capacitor C7 and effects a direct current I1. The elements of the circuit are designed such that the voltage U5 (and, therefore, the voltage U6 as well) lies in the modulation range of the amplifier OA1.

When $c_I$ becomes smaller and the capacitance $c_{II}$ becomes greater, then the voltage U1 at the time T1 rises in comparison to the value described above. The emitter current and the collector current as well therefore become greater; the current I1, smoothed via the capacitor C7, likewise becomes greater than the current I2, as a result whereof an input difference voltage is applied at the input of the amplifier OA1. Its output voltage U7 becomes more negative and the voltage U8 becomes more positive because of the inverting action of the amplifier OA2. As a result thereof, the emitter potential of the transistor T1 is increased via the resistor R8 and that of the transistor T2 is lowered via the resistor R7. The emitter current of the transistor T1 is diminished in that the emitter current of the transistor T2 increases. Due to the high open loop gain of the amplifier OA1, the voltages U7 and U8 are varied as long as the averaged currents I1 and I2 are again of the same size and the bridge therefore again achieves a stable condition.

The voltage difference between the voltages U7 and U8 required for this stable condition is a measure for the difference in capacitance between the capacitance $c_I$ and the capacitance $c_{II}$ and therefore represents the position of the buoyant member 1. The useful signal is the voltage difference between the voltages U7 and U8, whereby the smallest changes in capacitance are converted into great voltage increases.

The capacitors C3 and C4 reduce the influence of the dielectric constant E of the fluid to be measured, i.e., for example, of the fuel to be measured. Since the capacitors C1 and C2 in the illustrated embodiment lie fully in the fuel to be examined, their values are dependent not only on the excursion of the buoyant member but also on the dielectric constant E of the fuel. The sensitivity (output voltage difference per density difference) would therefore be greater given fuel having a higher dielectric value E. It can be shown that the influence of the dielectric value E disappears given a defined value of the capacitance of the capacitor C3 being equal to that of the capacitor C4.

Figure 4:
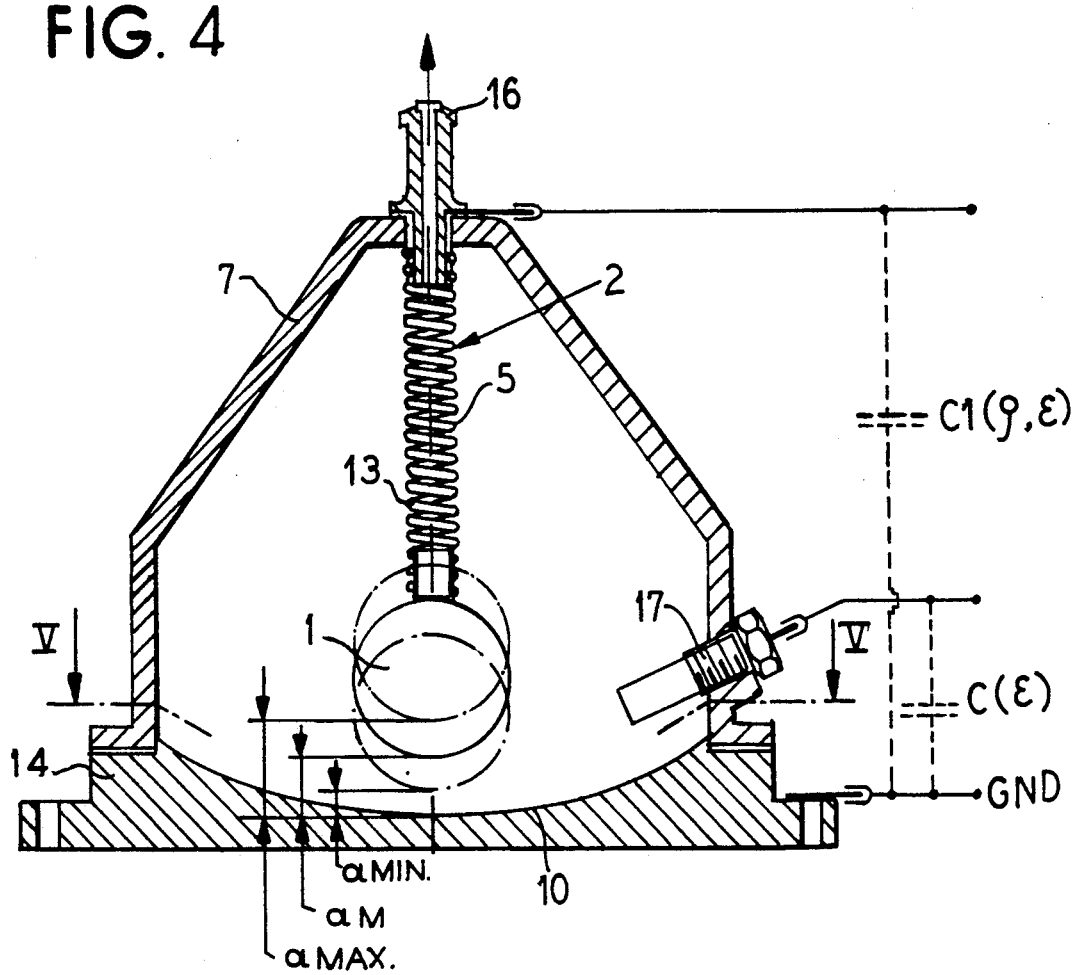
FIG. 4 is a vertical section taken through a structure corresponding to that of FIGS. 1 and 2 in another embodiment of the measuring device of the present invention.
Figure 5:
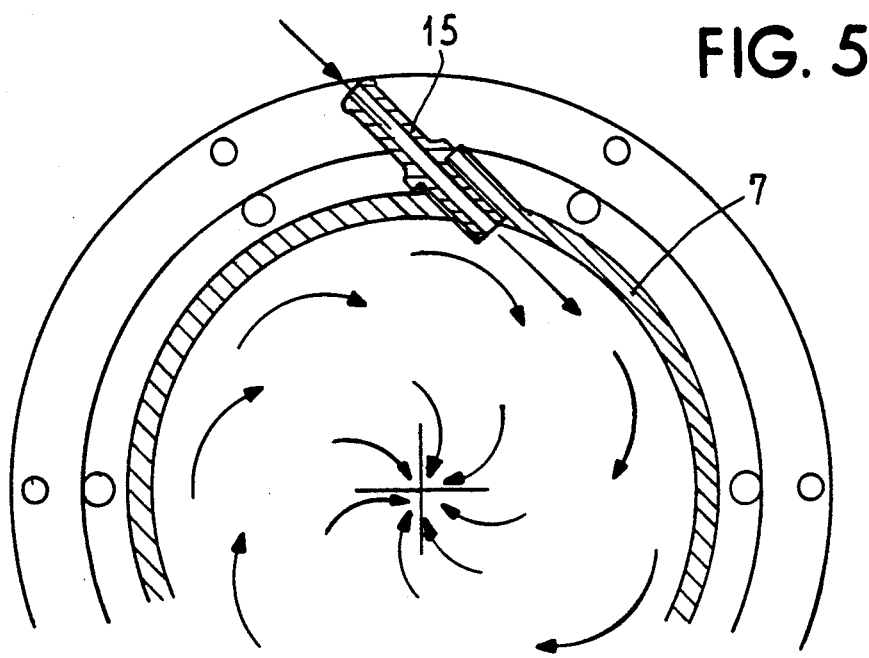
FIG. 5 is a sectional view taken generally along the parting line V—V of FIG. 4.

The arrangement of FIGS. 4 and 5 differs from the function of the corresponding arrangement of FIGS. 1 and 2 insofar as the spring 5 is now formed by a coil spring 13, is suspended in the upper region of the housing 7 and carries the buoyant member 1. The floor 14 of the housing 7 is closed except for the inlet 15 and outlet 16 for the fluid under examination. The outlet 16 forms the cooperating electrode of the capacitor C1 and is fashioned as a spherical cap having its center in the suspension of the coil spring 13. The inlet 15 for the emission of the fluid under examination is arranged tangentially aligned in the floor region of the housing 7. The outlet 16 lies in the uppermost region of the housing 7. It is therefore assured that the value of capacitance of the capacitor C1 remains the same and that a change in density is not erroneously indicated given lateral, slanting positions and excursions of the vehicle or the like that carries such a measuring device, this being assured as a consequence of the constant spacing between the buoyant member 1 and the cooperating electrode 10 at the floor 14.

In FIG. 4 a compensation electrode 17 is provided that is stationary relative to the housing 7 and that allows the dependency of the value of capacitance of the capacitor C1 on the dielectric constant of the fluid under examination in the housing 7 to be taken into consideration and that is likewise connected to the arrangement for monitoring the capacitance (for example, according to FIG. 3). The capacitance is therefore defined to ground as referenced at C in FIG. 4.

Figure 6:
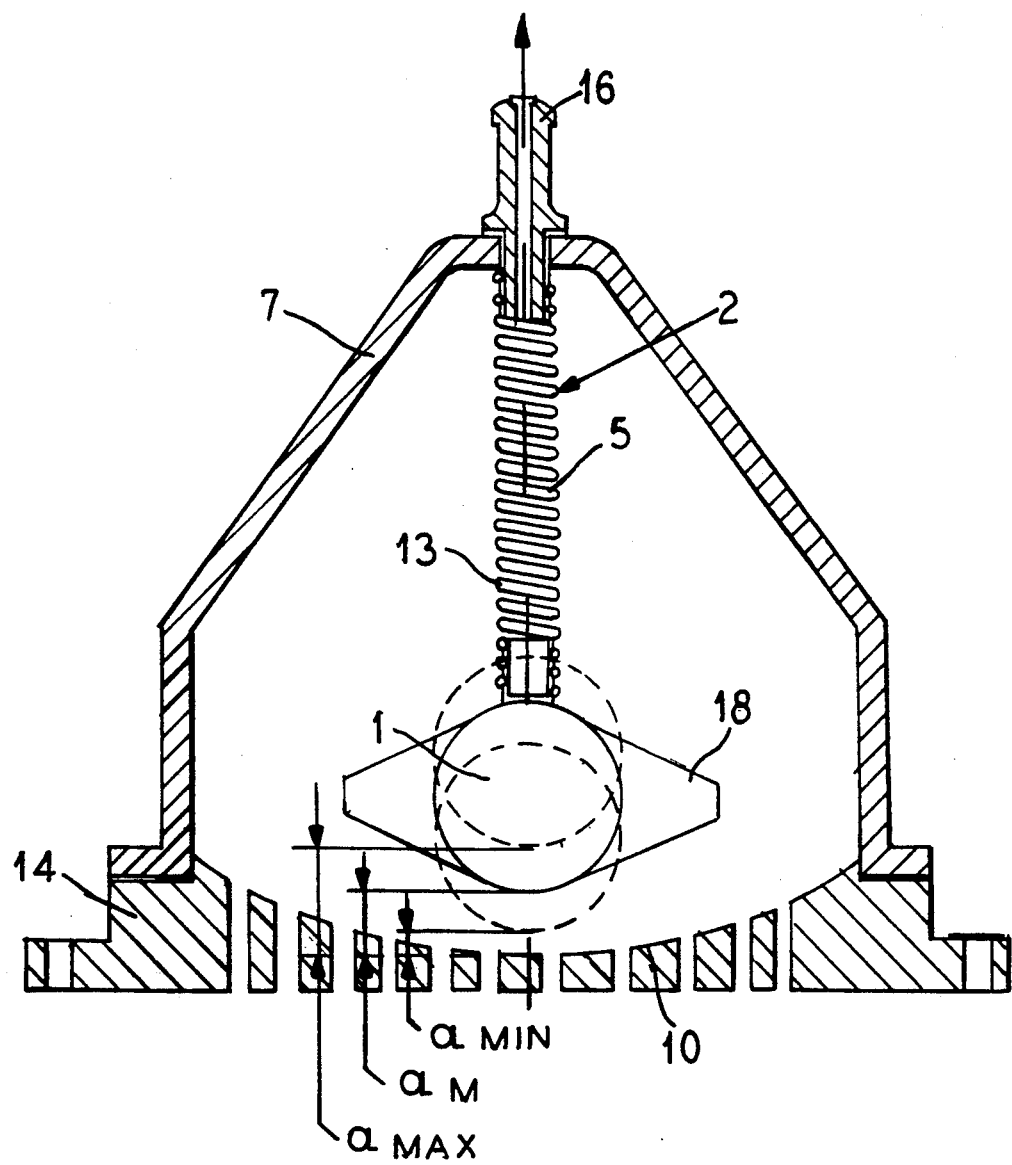
FIG. 6 is a vertical section taken through a structure corresponding to that of FIG. 4 in another embodiment of the measuring device of the present invention.

In FIG. 6 it is schematically illustrated that also be constructed directly as a sieve, instead of being fashioned with a tangential admission inlet 15 and could directly form the admission inlet proceeding from below for the fluid under examination. If necessary, further, the buoyant members 1 in both alternative embodiments under discussion could also be additionally provided with damping wings 18 so that undesirable movements are suppressed or can be further minimized.

Although we have described our invention by reference to particular illustrative embodiments thereof, many changes and modifications of the invention may become apparent to those skilled in the art without departing from the spirit and scope of the invention. We therefore intend to include within the patent warranted hereon all such changes and modifications as may reasonably and properly be included within the scope of our contribution to the art.

I claim:

1. An instrument for measuring the density of fluids, comprising:

a housing having a chamber with a vertical space to be filled with an electrically-nonconductive fluid to be examined;

a capacitor device variable in its capacitance and including said housing and a buoyant member in said housing chamber buoyantly movable vertically in the fluid; and load means for balancing the buoyancy of said buoyant member with a counterforce applying a balancing force increasing with change in position of the buoyant member, said load means including a spring in and connected to said housing and connected to said buoyant member;

said capacitor device functioning to indicate the position of the buoyant member to indicate the density of the fluid in the chamber.

2. The instrument of claim 1, wherein:

said spring is a leaf spring;

said housing includes a U-shaped carrier member holding said leaf spring and surrounding said leaf spring and said buoyant member, said U-shaped carrier member including a cooperative electrode of said capacitor device; and said buoyant member including a conductive vane extending adjacent said cooperative electrode and forming a movable electrode of said capacitor device.

3. The instrument of claim 2, wherein:

a perforate covering surrounds said carrier member.

4. The instrument of claim 3, wherein:

said perforate covering comprises a fine-mesh, electrically-conductive screen.

5. The instrument of claim 2, wherein:

said carrier member of said housing comprises a pair of spaced electrodes of said capacitor device; and said vane of said buoyant member forms a pair of differential capacitors with said pair of spaced electrodes.

6. The instrument of claim 1, wherein:

said housing includes an upper region and a lower region;

said spring comprises a coil spring suspended in said upper region;

said buoyant member is connected to and carried by said spring as a pendulum;

said housing is sealed and includes a floor in said lower region, a fluid inlet at said floor and fluid outlet; and said floor includes a spherical cap centered at the suspension of said spring and forming a cooperating electrode of said capacitor device.

7. The instrument of claim 6, wherein:

said fluid inlet is positioned to provide a substantially tangential fluid flow into said housing; and said fluid outlet is at said upper region of said housing.

8. The instrument of claim 6, and further comprising:

a compensation electrode mounted in said housing fixed spaced from said floor for taking the dielectric constant of the fluid into consideration.

9. The instrument of claim 6, and further comprising:

an oscillator circuit including a frequency-influencing component, said capacitor device connected as a part of said frequency-influencing component.

10. The instrument of claim 9, and further comprising:

damping elements on said buoyant member.

11. The instrument of claim 1, and further comprising:

a measuring circuit including a fed-back capacitive bridge circuit, said capacitor device connected in said fed-back capacitive bridge circuit.

12. The instrument of claim 11, and further comprising:

at least one compensation capacitor connected in said bridge circuit to suppress the influence of the dielectric constant of the fluid.

13. The instrument of claim 1, wherein:

said housing includes an upper region and a lower region;

said spring comprises a coil spring suspended in said upper region;

said buoyant member is connected to and carried by said spring as a pendulum;

said housing includes a floor in said lower region, a fluid outlet and a fluid inlet at said floor provided by forming said floor as a sieve; and said floor includes a spherical surface centered at the suspension of said spring through which passages of said sieve extend, said spherical surface forming a cooperating electrode of said capacitor device.

* * * * *